United States Patent [19]
Burnham

[11] Patent Number: 4,764,324
[45] Date of Patent: Aug. 16, 1988

[54] METHOD OF MAKING A CATHETER

[76] Inventor: Warren Burnham, 9964 Gansevoort Rd., R.D. #2, Fort Edward, N.Y. 12828

[21] Appl. No.: 845,492

[22] Filed: Mar. 31, 1986

Related U.S. Application Data

[63] Continuation of Ser. No. 743,890, Jun. 13, 1985, abandoned, which is a continuation of Ser. No. 560,526, Dec. 12, 1983, abandoned.

[51] Int. Cl.$^4$ .................. B29C 47/06; B29C 59/02
[52] U.S. Cl. .................... 264/103; 264/150; 264/151; 264/173; 264/174; 264/209.4
[58] Field of Search ............ 264/173, 103, 174, 150, 264/151, 209.4

[56] References Cited

U.S. PATENT DOCUMENTS

| | | | |
|---|---|---|---|
| 3,284,259 | 11/1966 | Galloway et al. | 264/173 |
| 3,558,754 | 1/1971 | Martin | 264/173 |
| 4,135,869 | 1/1979 | Foyer | 264/173 |
| 4,155,790 | 5/1979 | Galloway | 264/173 |
| 4,219,522 | 8/1980 | Oyama | 264/173 |

FOREIGN PATENT DOCUMENTS

| | | | |
|---|---|---|---|
| 1349843 | 4/1971 | United Kingdom . | |
| 1584616 | 2/1981 | United Kingdom | 264/173 |

OTHER PUBLICATIONS

File History of Seed, U.K. Spec. No. 1,584,616, published 26 May, 1978.

*Primary Examiner*—James Lowe
*Attorney, Agent, or Firm*—Ronald P. Kananen

[57] ABSTRACT

A process for making a reinforced tubular product, especially a catheter, in a single extrusion step. A reinforcing member is heated when applied to an extruded thermoplastic catheter body of about its finished size which is softened by heating while tensioning the reinforcing member to control the surface deformation or penetration of the catheter wall by the reinforcing member to produce an irregular surface contour on the catheter body. The catheter body is then smoothed in a sizing die burying the reinforcement to form the finished product. The heating step may be in addition to or substituted by a curing step when a thermosetting or crosslinking material is used for the body. The reinforcement may be braid, or a helical wrap of one or more members applied at one or more controlled angles relative to the axis of the catheter to control the strength and torque transmission efficiency of the catheter. The process is particularly adapted to making a catheter having its reinforcement interrupted to provide a unitary non-reinforced distal tip. By this process, the radial location of the reinforcement in the wall of the catheter is easily controlled according to the material of the body, the heating conditions, and the tension on the reinforcing member. Multiple extrusions to form a reinforced catheter body are thus not required.

35 Claims, 4 Drawing Sheets

U.S. Patent    Aug. 16, 1988    Sheet 1 of 4    4,764,324
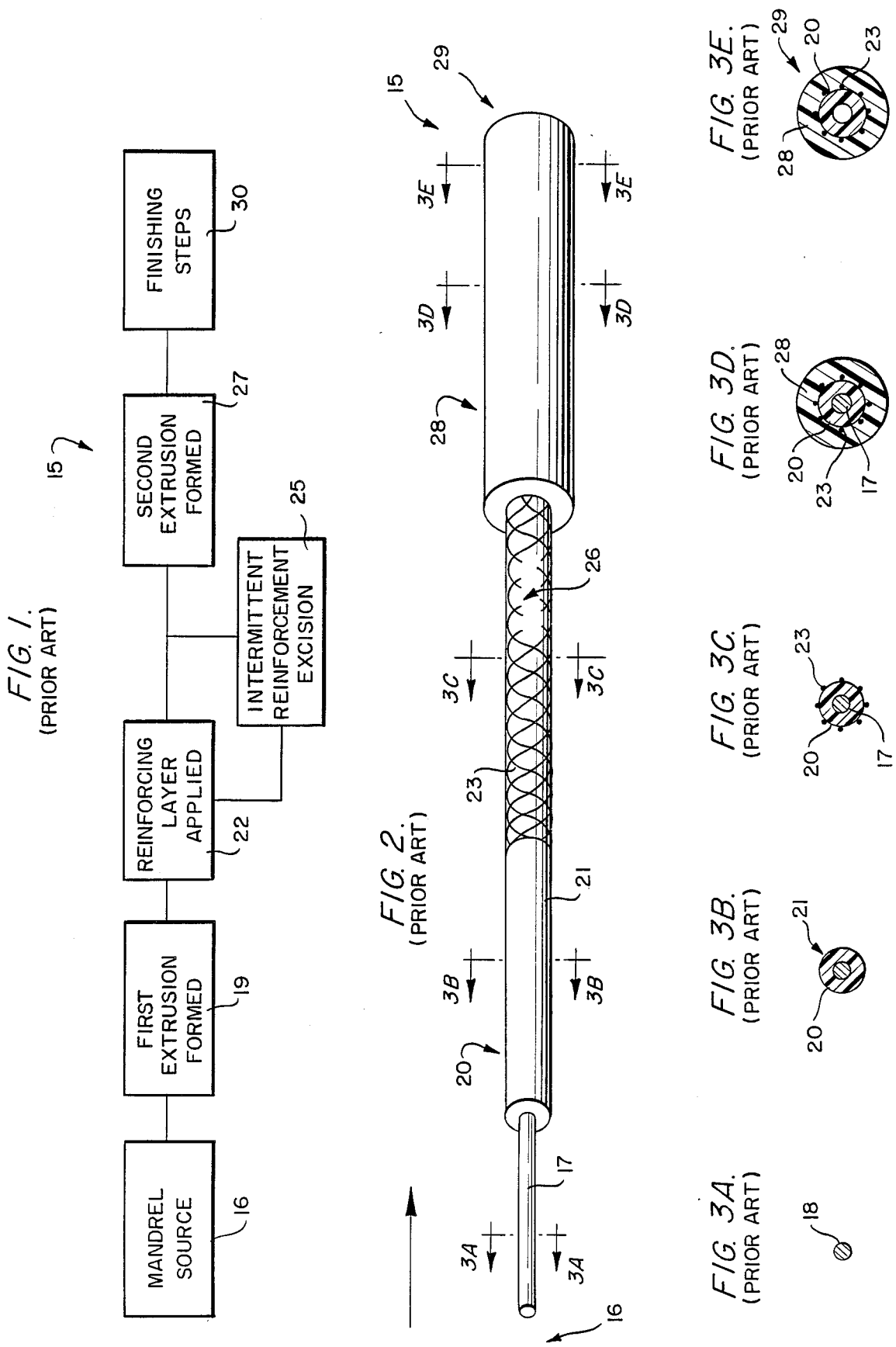

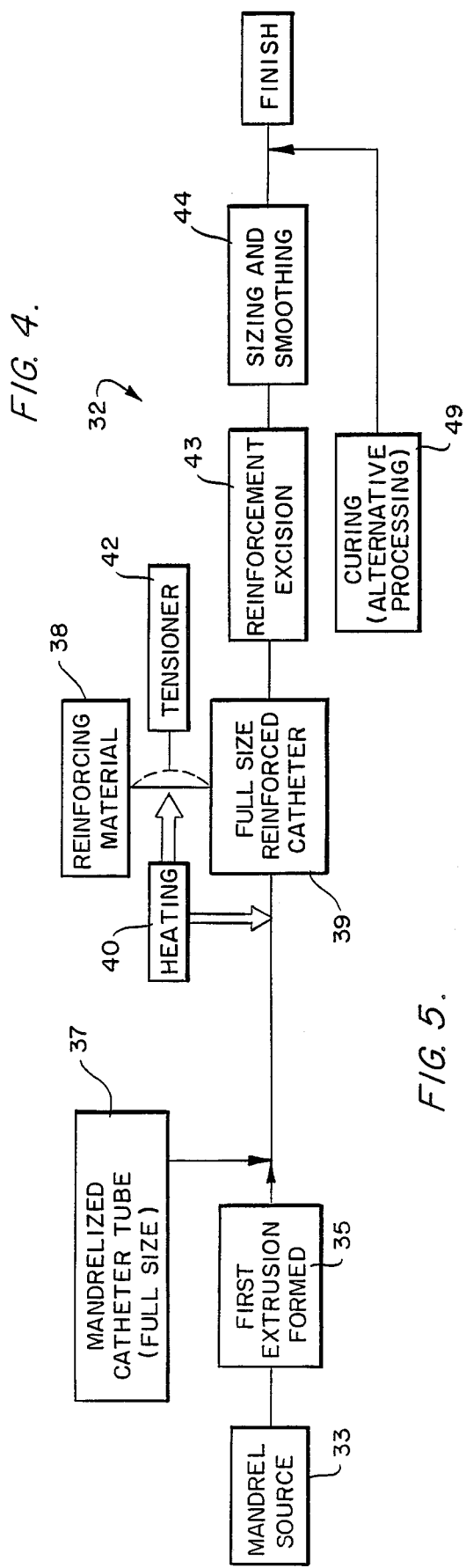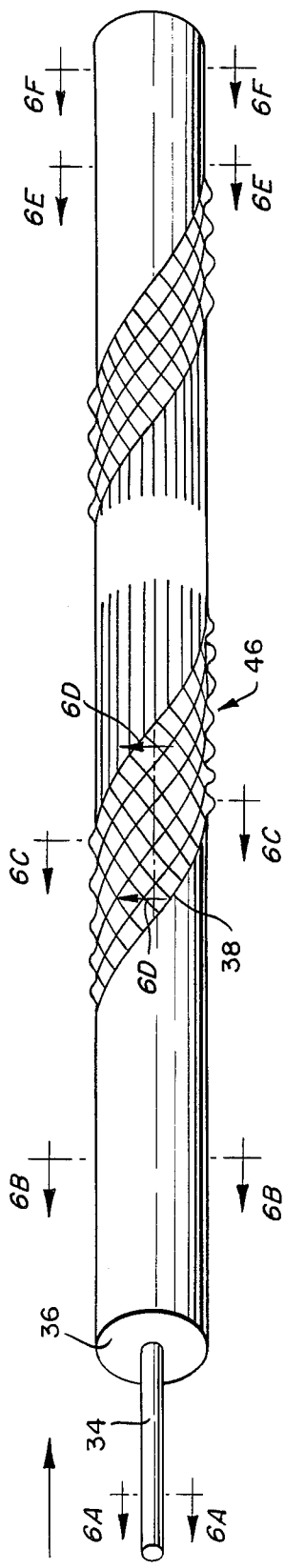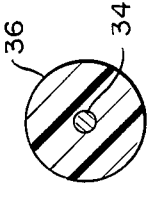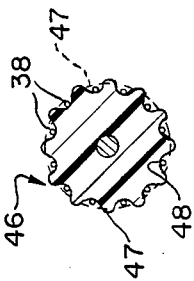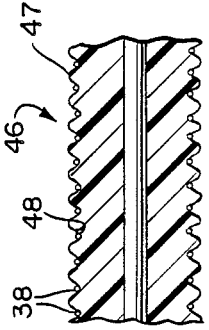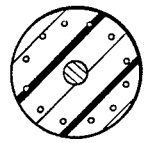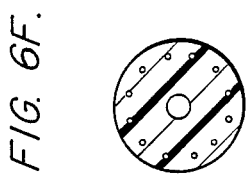

METHOD OF MAKING A CATHETER

This application is a continuation of application No. 06/743,890, filed June 13, 1985 which in turn is a continuation of Ser. No. 06/560,526, filed Dec. 12, 1983, both now abandoned.

BACKGROUND OF THE INVENTION

The present invention relates to a method of making tubular products, especially suited for the manufacture of catheters. More particularly, this invention relates to a method for making a reinforced tubular product, such as a reinforced catheter, in a single extrusion step wherein the location of the reinforcement in the wall of the tubular product is simply but accurately controlled. Still more particularly, this invention relates to a method for making a catheter of the type wherein the reinforcement is omitted from the distal end of the catheter through intermittent application of the reinforcement during the manufacturing process. Still more particularly, this invention relates to a method for making a reinforced tubular structure, such as a catheter, wherein the reinforcing material is applied by helically wrapping an intermediate structure with at least a length of reinforcing material and controlling the angle of helical wrapping to control selected physical characteristics of the finished product.

The art of manufacturing tubes, pipes or cannulae by extruding a plastic material to produce significant quantities of the tubing is fairly well developed. In many instances, it is desirable to use reinforcement in the tubes or pipes to increase the pressure, tensile, or torque carrying capacities of those tubes or pipes. Ordinary plastic garden hose reinforced with filament is a common example of such a product made according to prior art techniques.

A special type of tubular product, as is also well known in the art, is a catheter for application in the medical field. Catheters of the type contemplated are relatively thin and flexible tubes which include inner and outer plastic layers with a wire sheathing embedded between the layers. The wire sheathing is either braided or cross-wound to obtain a maximum torsional rigidity and a satisfactory longitudinal flexibility. However, such catheters and in particular those intended for diagnostic purposes, which use radio-opaque dyes and fluoroscopy, to deliver the radio-opaque dyes through the reinforced extruded catheter to the desired site have particular constraints on their construction. Since the dyes are relatively viscous, and the speed of injection is important, high pressures are developed in the relatively small tubing during delivery of the dye. To resist these high pressures, but to retain a degree of flexibility which permits the catheter to be used within a body, it is necessary to reinforce the flexible materials used in the catheter rather than use materials strong enough in their reinforced state. The latter materials are usually too stiff for use in the vascular system of the human body. Thus, in general, high strength tubes are too stiff for medical use, while highly flexible soft polymers have insufficient strength characteristics so that reinforcement of the softer materials with a higher strength reinforcing material is necessary.

All of the foregoing constraints are measured against the desirability in the art to make the outside diameter of the catheter, including its tip, as small as possible to reach very narrow passages in the body. In that regard, the flexible catheters produced according to the art, in addition to exhibiting satisfactory pressure resistance, must also be able to transmit axial torque from the end remaining outside of the body, i.e. the proximal end, to the other end of the catheter, i.e. the distal end, located inside the body. This torque transmission is required to allow the delivery tip of the catheter to be guided through the twists, turns, valves, and bends in the vascular system of a patient to arrive at the point where dye injection is desired. Such catheters generally have braided metal reinforcement in the wall of the small diameter catheters to withstand pressures of 1000 psi or more.

A typical prior art process for making a reinforced extruded catheter is a three step process. In the first step, a mandrel having an outside diameter equal to the desired inside diameter of the finished catheter is passed through suitable extrusion tooling to cause a tubular jacket or sheath of the catheter material to form around the mandrel. In this step, the outside diameter of the first extrusion layer on the mandrel is smaller than the desired finished outside diameter of the finished catheter. As an alternative, a non-mandrelized tube can be extruded with an ID and OD which are the same as that of the mandrelized tube. Next, the inner core tube formed in the first step as described above is processed by suitable machinery to cause a pattern of reinforcing material, such as wires, fibers, or monofilaments, for example, to be laid along and/or around and in contact with the surface of the core tube. Next, the composite intermediate structure of the inner core tube and the reinforcing layer thus applied is again passed through suitable extrusion tooling equipment to deposit a second layer of catheter material around and bonded to the composite thereby encapsulating the now-reinforced inner core tube forming essentially a single structure. The outside diameter of the second layer of extrusion is approximately equal to the desired finished outside diameter of the catheter. Subsequently, finishing and polishing operations can be performed and the composite thus constructed cut to its desired length. The mandrel, if any, is then extracted by lengthwise pulling, leaving the hollow catheter tubing with reinforced walls.

Most catheters require a flexible non-reinforced tubular tip on the end used in the body. Thus, a welding operation is then performed whereby non-reinforced tubing of similar overall dimensions to that of the reinforced body is added to the composite structure, such as by plastic welding. This provides a flexible tip for steering the catheter through the cavities in the body of the patient. It has, however, been a problem in the art that such weldments between the tip and the catheter body are sometimes weak causing the tip to break off during the catheterization procedure.

An advance in the method of manufacture is represented in U.S. Pat. No. 4,321,226 to Markling with regard to the manufacture of a tip wherein wire sheathing is omitted in the tip or distal end. The method there described provides for removing a portion of the wire braid through predetermined lengths of the catheter, such as by cutting, to leave defined, spaced, areas of the catheter without wire reinforcement for subsequent encapsulation by another extrusion. Thus, a unitary catheter, with an end portion without wire reinforcement adjacent to a portion with such wire reinforcement, is produced.

The art of applying braiding or multi-pass wire reinforcement to a catheter inner core is also well developed and machinery for performing such a step is well known. In general, such reinforcement material is applied to the inner core tube in a pattern of right and left hand helices, each having one or more reinforcements applied over a given area or length of the tube or cannula. However, a typical braiding process causes all reinforcements to be laid down in a direction which passes alternatively over and under all of the reinforcements laid down on the inner core tube in an opposite direction. Thus, the machinery performing the braiding process must move the reinforcements alternately radially inwardly and outwardly, as well as circularly, whereby the tension on the reinforcement continuously varies at a given production speed, and further increases as production speed increases. Such variations, in the extreme, cause the reinforcement to break, especially as the production speed increases. Moreover, the braiding machinery is subjected to significant internal inertial loads, shock loads, and lubrication requirements, especially because of the requirement to generate two directions of movement of the reinforcements at the same time. These shock and inertialloads put a definite upper limit on the speed of the machinery and therefore limit its production rate.

Still another shortcoming of braid-reinforced catheters arises from the oppositely-oriented application of the reinforcing braid resulting in difficulties in transmitting axial torque along the catheter while in use. When such a braided catheter is twisted, one of the helices of the wrap will be tensioned while the other is compressed, resulting in a loss of angular control through the catheter in steering the catheter through the human body, due to inefficiencies in transmitting torque through the elongated catheter body.

Still another difficulty with prior art catheters results from the inherent compromise between stiffness and torque transmission due to the helix angle of the braid. As the helix angle (i.e. the angle of the reinforcement relative to the axis of the catheter) decreases, the apparent stiffness of the catheter increases, but the efficiency of torque transmission decreases. Thus, a tube or catheter with wire parallel to its axis yields the maximum stiffness but the minimum torque transmission efficiency; conversely, a circular wrap has not only the highest torque transmission efficiency but also the poorest stiffness characteristics. Thus, the angle of helical braid generally selected in conjunction with the polymer used is a compromise between these two factors and thus limits the polymers which may be used. It is an aim of the invention to utilize a wrapping technique for applying reinforcement at a high angle (i.e. nearly circular wrap) while also applying a second wrap at a lower angle (more axial) to make integral tip catheters with soft polymers previously unsuitable for use in catheters.

Thus, it is an overall objective of this invention to provide a reinforced catheter of the type described in which the reinforcement materials are provided on an intermittent basis along the body of the catheter and wherein the radial location of the reinforcement layer in the wall of the catheter is precisely controlled, while at the same time reducing the number of steps in the production process.

It is another objective of this invention to provide a method for making a catheter by heating a catheter tube and a reinforcing member while tensioning the member as the reinforcing member is applied to the tube, so that the member deforms or penetrates the softened tube wall to a depth controlled by the degree of tensioning and the plasticity of the tube, whereby, after smoothing and sizing, a single extrusion of a tube at essentially the finished size can produce a reinforced composite catheter.

It is another overall objective of this invention to produce a tube by the process described wherein the pattern of the reinforcement is interrupted to provide a straight line of reinforcement at the surface of the tube to permit easy removal of such straight portion when producing, for example, an integral tip catheter.

It is still another objective of this invention to apply a helical wrap to a body of tubular material at a large angle approaching a perpendicular to the axis of the tube and applying a second helical wrap at a small angle approaching the axis of the tube, whereby torque and stiffness of the tube are maximized while expanding the class of polymers which may be used.

These and other objectives of this invention will become apparent from the drawings and the detailed description of the invention.

SUMMARY OF THE INVENTION

The applicant's invention is bottomed on the discovery that by heating the reinforced material and the polymer substrate beneath it during a process of manufacturing a catheter while simultaneously applying axial tension to the reinforcement, the reinforcement material, whether it is a braid, wire, helical wrap, or the like, will be caused to deform or penetrate the original surface of the catheter body polymer and thus to sink into such surface. In practice, it has been found that the distance into which the reinforcement material sinks into the underlying polymer is highly controllable and repeatable depending on the conditions of the relative temperatures of the catheter body and the reinforcement material, as well as on the tension exerted on the reinforcing material. Thus, by controlling these three parameters, the radial position of the reinforcement in the wall of the catheter can be simply but accurately controlled.

Following the submersion of the reinforcing material into the catheter-polymer body, the polymer thus softened and deformed or penetrated, but remaining outside of the new smaller diameter of the reinforcement structure, produces a somewhat peaked or waffled contour in those locations where the polymer has exuded between the strands or filaments of the reinforcement and extends radially outwardly beyond the reinforcement to an extent where it can be worked to form the outer wall of the catheter body without a second extrusion of the catheter wall as in a prior art process. This second significant feature of the applicant's invention permits a reinforced catheter of the type described to be produced in a single extrusion step followed by a single finishing step, rather than a multi-step extrusion process insofar as the production of the catheter walls is concerned. The peaked, exuded, or waffled contour of the composite reinforcement catheter-polymer construction is then caused to pass through a sized opening in a contour die so that the protrusions of polymer there present are caused to flow in a way to fill the valleys caused by this submersion of the reinforcement material into the polymer wall. Thus, a smooth surface composite construction of polymer containing the embedded reinforcement below the now smooth surface is thus produced. It can thus be seen that a major point of significance in the invention resides in the fact that it eliminates the necessity for multiple extrusions of polymer layers as is now required to build a reinforced polymer composite.

With the composite reinforced catheter body construction produced according to the process described, the reinforcement material may be intermittently applied on and into a single layer of polymer to produce a catheter body in which the distal tip is integral with the catheter body but is devoid of reinforcement to permit the desired flexibility for the tip. In this process, the reinforcement material is applied by submersion through a single layer of polymer extrusion and the pattern of application interrupted into a straight line pattern which is not submerged into the catheter wall body. The straight line, non-submerged, reinforcement structure is then removed so that by using a smoothing die, a non-reinforced section remains, thus forming a unitary catheter tip.

In the alternative, the application of the wire braid or reinforcement material by a wire braiding machine, or machine for reinforcement of the type known to the art into the outside surface of the extrusion of the catheter wall about the mandrel is periodically interrupted at predetermined lengths to lay down on the outside diameter of the catheter wall a series of straight line wires which are cut and removed prior to the application of the outer covering. This provides the catheter with a reinforced area followed by a non-reinforced area which is the desired end result in the terms of the use. Thus, the tip of the catheter is extremely flexible, while the remaining portion of the catheter is reinforced.

Another significant feature of the invention for producing a catheter of the type described resides in the fact that conventional braiding for the reinforcement material may be replaced with helical wrapping as described in detail. The application of reinforcement to tubes with the use of helically wrapped right and left hand reinforcing materials, sequentially applied instead of woven or braided reinforcing materials, for pressure resistance and torque transmission in tubes or cannulae, is known. However, such reinforcements are usually installed in tubes, pipes or cannulae in a pattern of right and left hand helices consisting of one or a plurality of reinforcement strands applied over a given area of length of the tube or cannula.

Another feature of the invention resides in the application of a first helical wrapping at a large angle relative to the axis of the underlying tube and a second wrap at a small angle relative to the axis. The application of a multiple set of reinforcements produces tubes or cannulae with precise torque and stiffness thus allowing a broader range of polymers with their broader range of physical properties.

These and other features will become apparent from the description of the drawings and the written description of the invention which follows.

BRIEF DESCRIPTION OF THE DRAWINGS

In the drawings:

FIG. 1 is a block diagram of a prior art process for manufacturing an intermittently reinforced catheter with an unitary reinforced tip;

FIG. 2 is a pictorial diagram, partially in perspective, showing the catheter structure as it progresses through the manufacturing process diagrammed in FIG. 1;

FIG. 3, including FIGS. 3A-3E, are cross sections of the composite catheter structure at various steps in the prior art process depicted in FIGS. 1 and 2;

FIG. 4 is a block diagram of the process according to the invention;

FIG. 5 is a pictorial diagram, partially in perspective, showing the structure of the invention at various stages in the manufacturing process of FIG. 4;

FIG. 6, including FIGS. 6A-6F, illustrates cross sections of the composite structure at various stages in the process shown in FIGS. 4 and 5 according to the invention;

DETAILED DESCRIPTION OF THE PREFERRED EMBODIMENTS

Figure 7:
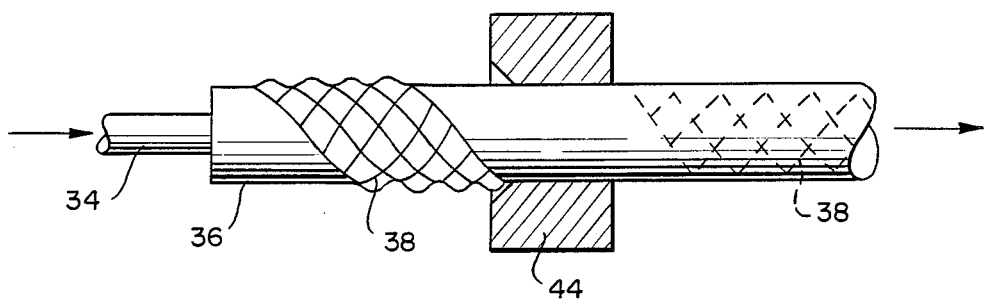
FIG. 7 is a side elevational view, partially in block form, showing the reinforced composite single layer catheter passing through a sizing die to smooth the outer surface to produce a finished catheter.

FIGS. 1-3 describe in greater detail a prior art process for manufacturing a reinforced tube, for example, a catheter, as designated generally by the reference numeral 15. As shown in FIGS. 1-3 a mandrel 17, from a mandrel source 16, comprises an elongated tubular or solid form 17 having a generally circular cross section 18 (FIGS. 3A) is passed through an extruder 19 to provide a sheath 20 of plastic material about the mandrel 17. The mandrel 17 has an outside diameter equal to the desired inside diameter of the finished catheter 15. The innermost layer of the catheter wall is formed from the sheath 20 to form a core tube for the finished catheter and has an inside diameter equal to the outside diameter of the mandrel 17. The plastic sheath 20 about the mandrel 17 during the first extrusion step has an outside diameter which is smaller than the desired finished outside diameter of the finished catheter. As an alternative, a non-mandrelized tube can be extruded with an inside diameter and outside diameter which are the same as that of the thus-mandrelized tube. In such a process, the plastic is usually a thermoplastic material exhibiting a range of apparent viscosity proportional to temperature, although other materials such as vinyl or rubber may be used, and machines for extruding such materials as a sheath are known.

The inner core tube 21 formed as described above is processed by suitable machinery 22, known to the art, to cause a pattern of reinforcing material 23 to be laid along and/or around and in contact with the outer surface of the core tube 21. By way of example, the reinforcing material may include wires, fibers, monofilaments, or braiding. Where desired, the composite catheter structure with the reinforcing material 23 may be processed to intermittently excise a portion of the reinforcement, as shown generally by step 25. In performing this step, the reinforcement material thus formed is physically removed along spaced portions of the core tube 21, as shown at portion 26 of FIG. 2. Thereafter, the core tube 21 with reinforcement spacedly excised is passed again through an extruder 27 to form a second layer 28 of extruded wall material as a sheath and bonded to the composite to produce a composite structure having an outer diameter approximately equal to the desired finished outside diameter of the catheter. In performing this step, therefore, the reinforcing layer 23 (whether or not partially excised) is thus embedded in the wall of the final composite catheter structure 28, which wall comprises two radially located sequentially applied extrusion layers bonded together to form a structurally single tube wall. Finally, in the step designated generally by the reference numeral 30, the composite thus constructed may have its wall smoothed to a tolerance of about ±0.0005 inches; is cut to its desired length; and the mandrel 17, if used, is extracted by lengthwise pulling leaving the hollow catheter tubing with intermittent or continuous reinforced walls.

The process for making the tube, such as a reinforced catheter, according to the invention is best seen in its preferred embodiment in FIGS. 4–6. In FIG. 4, the process according to the invention is designated generally by the reference numeral 32. As a starting material for the process 32, a mandrel 34 from a mandrel source 33 is passed through an extruder 35 to deposit a sheath 36 about the mandrel 34 in a manner somewhat similar to the first extrusion step of the prior art. However, the outside diameter of the extrusion here is approximately equal to the full outside diameter of the finished catheter. In the alternative, a full size mandrelized catheter tubing may be provided, as representatively shown in block 37, and used as a starting composite for further processing according to the invention wherein the catheter tubing has an outside diameter approximately equal to the final outside diameter of the finished catheter.

Reinforcing material 38 is applied to the mandrel/tubing composite structure 39 in a manner similar to that described in connection with FIG. 1. However, it has been found that the application of heat by a suitable heat source 40 to the mandrelized wall tubing acting as a starting material and/or to the reinforcing material 38, and preferably to both, while simultaneously tensioning the reinforcing material by a tensioning device 42 will cause the reinforcing material when applied to the original surface of the catheter body to sink into such surface and to penetrate or deform it. The heat thus applied to a thermoplastic material forming the catheter body causes the thermoplastic polymer to soften to an extent sufficient to permit such penetration or deformation.

It has been found that the distance into which the reinforcement material penetrates beneath the surface of the catheter body and thus sinks into the underlying polymer is highly controllable and repeatable. That distance is a function of the relative temperatures of the catheter body and the reinforcement material, as well as the simultaneous tension exerted on the reinforcing material by the tensioning device. Thus, by way of example, if the temperatures applied to the catheter body and the reinforcement material are controlled within toleranced limits, for a given catheter body made from a known polymer exhibiting known viscosity as a function of temperature, the depth of penetration of the reinforcing material can be determined for a given process rate and time of application virtually solely by the degree of tensioning applied by the tensioning device.

In an alternative practice of the invention, assuming that the tensioning is fixed within toleranced limits, the degree of heating of the catheter body and/or the reinforcement material, but preferably the former, will similarly control the depth of penetration at a constant process speed. In its simplest form, controlling the temperature of the heat source 40 will control the degree of heating of the catheter body composite at that stage in the process. Since the process is practiced on a continuous basis, the heating temperature may also be controlled by the speed of the process, by way of example, by passing the mandrelized catheter body through a heat source 40 providing a source of heat within toleranced limits. A representative way of applying heat to the catheter body 36 is by passing the catheter body 36 through an oven, or through a fluid heat transfer medium for a time sufficient to permit the catheter body 36, or at least the radially-outwardly extending portion of the catheter body 36, to soften to an extent which permits it to receive the reinforcing material 38 therewithin.

Such a process had significant advantages in controlling the placement of the reinforcement material 38 in the wall of the catheter body and thus is particularly suited for applications in which it is necessary to structure a catheter such that the reinforcing material 38 is located near the outer wall of the catheter, near the inner wall of the catheter, or at a precisely-controlled selected point in between. When it is remembered that catheter bodies are extremely small structures and catheter walls are extremely thin, such a process has significant advantages in assuring that the reinforced materials are embedded within the catheter wall throughout the length of the catheter while at the same time omitting the second extrusion step as previously discussed in connection with FIG. 1.

FIG. 5 and FIGS. 6A–6F further illustrate the features of this aspect of the invention. Following the submersion of the reinforcing material 38 into the catheter body made from a thermoplastic polymer, the polymer thus softened and penetrated, but remaining outside the new smaller diameter of the reinforcement structure, produces a peaked or waffled contour, designated generally by the reference numeral 46 (FIG. 6C) in those locations where the polymer has exuded between the penetrating strands of the reinforcing material 38. The volume of polymer material from the reinforcement structure which is displaced is about equal to the volume of the reinforcing material 38 submerged in the catheter body. Thus, in FIG. 6C, the outside diameter of the composite catheter prior to application of the reinforcing material is designated by a dotted line by the reference numeral 47 to illustrate that in general the peaked areas 46 extend beyond the former outside diameter of the catheter body, while the valley areas formed near the wire (designated generally by the reference numeral 48) generally inwardly peak at the location of the reinforcing material 38 at a radially outwardly extending distance less than that of the former outside diameter 47 of the catheter body. Such a formed structure is advantageous in that in subsequent processing, the protruding portions 46 may be smoothed over in a sizing and/or smoothing step 44 to form a smooth catheter wall completely enveloping and embedding the reinforcement material 38 as seen in FIGS. 6E and 6F. More significantly, such a step avoids the application of a second extrusion.

Returning to FIG. 4, the composite structure with the waffled contour as shown in FIG. 6C, if desired, may be processed to intermittently excise a portion of the reinforcement 38 to form a unitary catheter or alternatively, where intermittent reinforcement is not desired, to pass directly to a sizing die for smoothing the outer wall to make the final product. In the sizing die, the protrusions 46 are caused to flow in such a way as to fill the valleys 48 caused by the submersion of the reinforcement material 38 into the polymer wall 36. Thus, a smooth surface composite construction of a polymer containing the embedded reinforcement material 38 below the now smooth surface 49 is thus produced. Thus, the sizing and smoothing step 44 in the process is shown in greater detail in FIG. 7.

Figure 8:
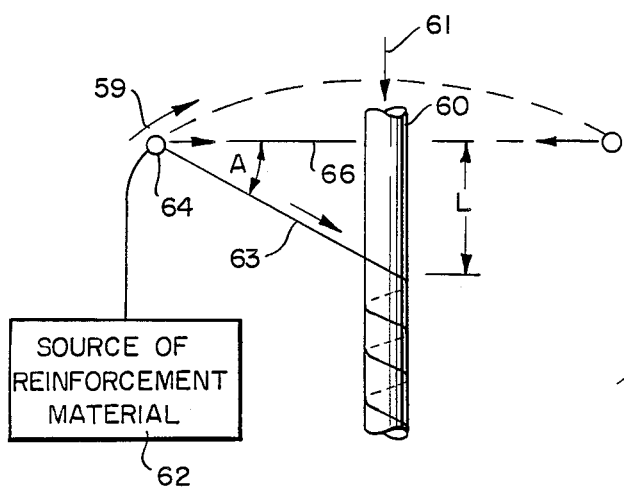
FIG. 8 illustrates in diagrammatical form the step of helically wrapping reinforcement material about a tube.
Figure 9:
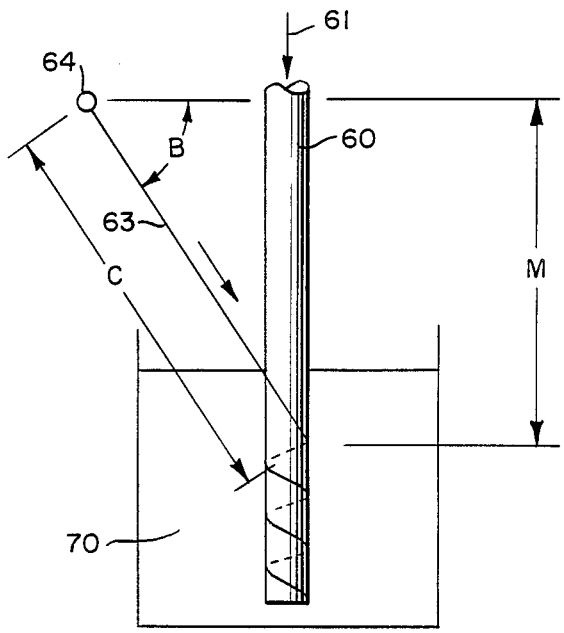
FIG. 9 is a view similar to FIG. 8 illustrating the intermittent helical wrapping of the composite catheter structure to permit excision of intermittently spaced portions of the reinforced portions of the reinforcement remaining on the surface of the tube to produce a unitary catheter.
Figure 10:
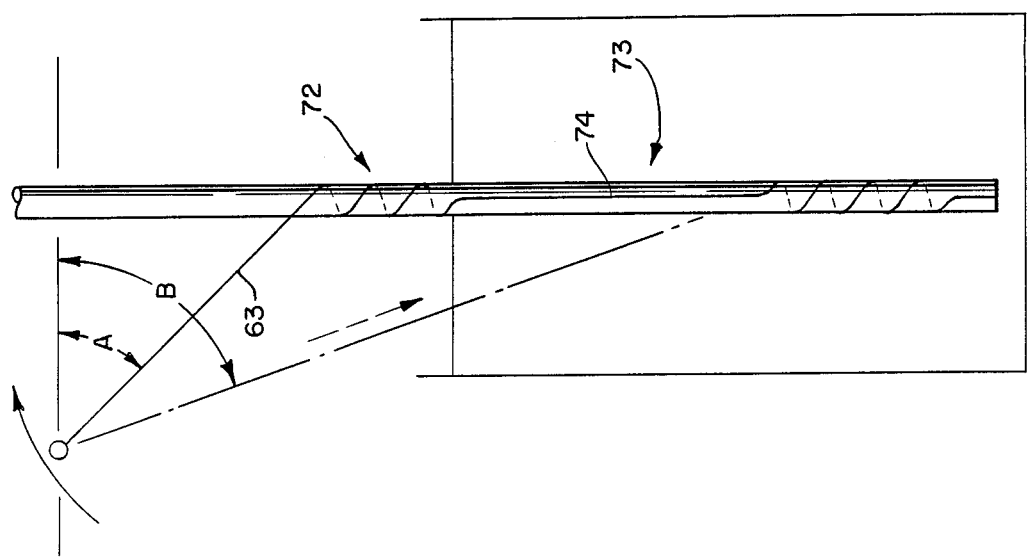
FIG. 10 is a view similar to FIGS. 8 and 9 showing the laying of material on or near the surface the tube or cannula and adjacent to embedded reinforced sections of the catheter.

In the process according to the invention, the composite reinforced catheter body construction produced according to the invention may have the reinforcement material intermittently applied, as in the prior art, or by continuously applying the reinforcement material and then excising portions thereof, or by periodically stopping the application of the reinforcement material, or continuously applying the reinforcement but in such a way as to cause the reinforcement material to lie along the outer surface of the composite structure as a series of straight line strands as shown in FIG. 5 and in FIGS. 8-10 as will be explained in greater detail. Such a straight line pattern is not submerged into the catheter wall body and thus easily removed from the surface of the composite structure so that upon smoothing in a smoothing dye, a non-reinforced section remains, thus forming a unitary catheter tip.

The process of the invention may be performed continuously utilizing conventional machinery. Thermoplastic polymer mandrels, extruders, and machines for applying reinforcing material, such as braiders, are known to the art. For example, braiding machines are available from either New England Butt Company or Wardwell Company, by way of example.

As specific examples of the type of thermoplastic plastic materials which may be used, such materials include polyethylene, polyurethane, certain rubbers, latexes, and vinyls, conventionally available from such companies as DuPont. Presently, for catheter construction, urethane thermoplastic materials are preferred. As a specific example of a preferred reinforcement material, one may use polyaramid, which is commercially available under the trademark "KEVLAR", but other materials such as carbon boron fiber, glass, ceramic, non-metallic wires, metallic wires (DBS), and natural fibers such as cotton, as well as monofilaments such as nylon and polyester, may also be used. Where it is desired to utilize the reinforcement material as a conductor for signals, an electrically conductive wire may be used as all or any part of the reinforcement material.

The embodiment of FIG. 4 has been described with respect to thermoplastic polymers forming the catheter body, using heat as the medium for controlling the plasticity of the wall to permit penetration of or deformation by the reinforcing material to form the waffled contour 46. In the alternative, as shown by the step bearing the reference numeral 49, other curable polymers may also be used. Where, for example, the polymer may be hardened by curing by cross-linking under the application of ultra-violet light, or by ionizing radiation, a curing step particular to the curable resin may be used. Such curable polymers may possess a sufficiently semi-rigid body characteristic prior to curing to permit penetration into, or deformation of, the surface by the application of the reinforcement material, as previously described, or to form the waffled contour without the application of heat as described in connection with FIG. 4. In those instances, the step of applying heat may be eliminated in favor of a curing step after the application of the reinforcement material and/or its partial excision as described and during or after sizing as shown in step 44. These alternative times of application of the curing step subsequent to the application of the reinforcement material to the catheter body being formed are designated generally by the two arrows connecting the block 49 to the process of FIG. 4. However, depending on the characteristics of the material used, a curing or partial curing step may be carried out either earlier or later in the process while carrying out the essential features of the invention.

Again depending on the material used, it also may be desirable to use a combination of the heating step 40 to soften the body of a curable material, followed by the excision, sizing, and smoothing, and by curing steps to cure and harden the polymer, such as by ultra-violet light, radiation or the application of a curing agent to the material to harden its structure to a condition suitable to its end use.

Another significant feature of the invention relates to the intermittent reinforcement for tubes or cannulae wherein the reinforcement is not continuous, while the tube or cannula is continuous yielding a tube or cannula with reinforced and non-reinforced areas sequentially spaced in any desired combination of space of reinforced and non-reinforced sections along the tube.

As thus seen in FIGS. 8-10, a tube or cannula 60 moving in the direction designated generally by the arrow 61 in the process of FIG. 4 is reinforced by the helical application of a reinforcement material 63 passing through a rotating guide 64 from a source of reinforcement material 62. As the guide 64 rotates around the tube or cannula, as designated generally by the arrow 59, while guiding the reinforcement material 63 to be wrapped about the tube 60 which is advancing in the direction of the arrow 61, the reinforcement assumes an angle A which is also the helix angle of the reinforcement in the tube 60. The angle A is the result of the ratio between the number at turns around the tube to the distance the tube advances during those turns. This results in a length L between the plane of rotation of the guide 64, defined by the path of the arrow 59, designated generally by the reference numeral 66 as the tube advances in the continuous process.

As shown in FIG. 9, if the guide 64 carrying the reinforcement 63 stops rotating about the tube 60, but the tube 60 continues advancing in the direction of the arrow 61, the reinforcement 63 assumes an angle B which constantly increases as the tube advances thus approaching, but never reaching a true parallel condition with the axis of the tube 60. Under these conditions, a length M of the tube which is not wrapped with reinforcement is caused to form and the length M will continue to increase while the rotation of the reinforcing guide 64 is stopped. If a cooling medium, for thermoplastic resins, or a curing material for a curable resin, or for thermosetting or other curable polymers, is provided at the location defined by the length M, the advancing tube or cannula 60 carries the last area of wrapped reinforcement into an environmental structure 70 causing solidification of the tube prohibiting further embedding of the reinforcement therein. In addition, as the angle B increases, the four force vectors of the tension on the reinforcement reduce the pressure to cause embedment according to the relationship F=T B. Thus, after the desired length M is developed, to define the wrapped length followed by the unwrapped length, wrapping or braiding resumes (as in FIG. 10) causing the resumption of the angle a defining the length L which is outside of the area of cooling or curing, thus allowing resumption of the embedding process in the soft or uncured polymer. In addition, the last end of the straight unembedded reinforcement is captured when embedding restarts.

As best seen in FIG. 10, as a result of the starting and stopping of the wrapping and braiding operation, the reinforced tube or cannula 60 thus generated has areas 72 of helically wrapped or braided embedded reinforcement 63 sequentially followed by lengths 73 of tube or cannula in which the wrap or braid is not embedded within the wall of the structure but rather is laying on or near a surface of the tube or cannula, as designated generally by the reference numeral 74. Therefore, as a subsequent operation to the reinforcement application, the straight loose reinforcement thus positioned can be cut away or removed so that upon final finishing, as described in connection with FIG. 4, that portion of the tube or cannula is unreinforced while the remainder of the tube or cannula is reinforced.

An advantage in using the helical wrapping process of the type described in connection with FIGS. 8–10, in addition to its convenience for removing the reinforcement, is that the machinery to perform such an operation only rotates the reinforcement in smooth circles, as understood from the plane 66 generated by the path 59 of rotation shown in FIG. 8. Thus, no tension changes in the reinforcement or inertial shock loads in the machinery result. Thus, the only significant practical limits on the speed of production are the structural loads of the centrifugal force on the bearings and components, thus resulting in a speed increase over braiding of a factor of four or more. In addition, a catheter utilizing such a process avoids the problems described in efficiently transmitting the torque through the catheter during the use procedure. As can be seen, the transmitted torque takes the form of tension in the appropriate reinforcement. The tensile torque thus acts in a straight line parallel to the axis of the reinforcement material since the reinforcement material is supported by the substrate. In the braided structure, as in FIG. 1, for example, where the reinforcement is in a zigzag pattern caused by its alternate passage over and under other reinforcements, the tension force in the reinforcement first tries to straighten the reinforcement back into a straight line before transmitting the remaining torque. This operation is somewhat similar to the step of "taking up slack" required by a plurality of zigzag patterns in a sample length of braided reinforcement and thus causes a sponginess or need to overtwist the structure to cause the distal end to rotate in the desired amount.

On the other hand, according to this process of helically wrapping the reinforcement structure, the tension forces caused by twisting are transmitted axially down the reinforcements by the shortest possible path increasing the efficiency of torque transmission through the catheter structure. Such torque losses as exist are thus caused primarily by substrate deflection and are common to both braided and wrapped structures. Accordingly, torque transmission efficiency through the thus-wrapped catheter is improved significantly.

Figure 11:
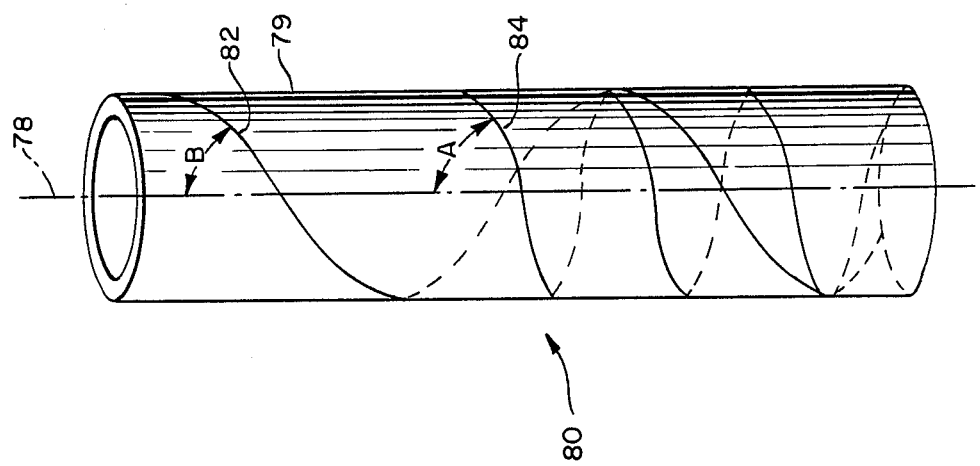
FIG. 11 is a diagrammatical view of a multiply wrapped catheter according to the invention.

FIG. 11 shows still another aspect of the process according to the invention which utilizes a plurality of wrapped reinforcement structures, designated generally by the reference numeral 80. By using the wrapping technique of applying reinforcement, it is possible to apply reinforcement 82 at a low angle B to the axis 78 approaching circular patterns parallel to the axis 78 of the tube 79, while also simultaneously or sequentially applying another set of reinforcements 84 at a high angle, i.e. at an angle more closely normal to the axis 78. The double set of reinforcement helices from the plurality 80 thus produced allows the design of tubes or cannulae with precise torque or stiffness characteristics, while also using a broader range of polymers than heretofore have been unable. This step allows the making of integral tip catheters with tip portions which are softer than those known to the art since there is less consideration given to the polymer stiffness in making the body or "shank" of the catheter. Thus, in FIG. 11, the reinforcement material 84 is applied at an angle A responding to the torque and pressure reinforcement requirements of the catheter, while a second reinforcing helix is applied at an angle B. The numbers and angles of both types of reinforcements with respect to the axis are variable with respect to each other and with respect to the axis of the tube or cannula, resulting in a significant flexibility in tuning the desired characteristics of the catheter to those which produce the features sought.

Thus, an improved method of making a reinforced tube or catheter is described.

What is claimed is:

1. A continuous method of making a finished reinforced catheter made from a polymeric material exhibiting a range of apparent viscosity proportional to temperature and having an inner diameter and an outer diameter with reinforcement completely embedded within the wall of said catheter between said inner diameter and said outer diameter with a single extrusion step and without internal application of external pressure, comprising the steps of:

providing as an interim structure an extruded, mandrelized polymeric catheter body having an outer diameter about equal to the outer diameter of the finished catheter;

providing said mandrelized catheter body in a condition heated to a state sufficient to permit a reinforcing member under tension to be submerged completely beneath an outer surface of the heated tubular structure;

applying said reinforcing member at the outer surface of said heated interim mandrelized catheter body under sufficient tension to cause said reinforcing member to travel inwardly through said polymeric outer surface to a predetermined extent to deform said outer surface relative to the reinforcing member by a volume about equal to the volume of said reinforcing material added to said tubular structure and to locate the reinforcing member accurately in the wall of said body thus defining wall portions which lie radially outwardly and inwardly of the former outer diameter of the catheter body, a combination of the temperature and said polymeric material of said interim catheter and tension on said reinforcing member controlling said predetermined extent, the location of said reinforcing member within the finished product being defined by the location of said reinforcing member when applied to said interim catheter body; and smoothing said deformed outer surface to form said catheter with the reinforcement member precisely located within the wall of the catheter without further extruding a plastic material thereon to form said finished, catheter reinforced.

2. The method of claim 1 wherein said catheter is made from a thermoplastic resin, and the step of applying includes the step of heating said mandrelized catheter body to a degree which sufficiently softens the catheter body to permit deformation or penetration when said reinforcing member is applied thereto.

3. The method as set forth in claim 2 wherein the step of heating further includes the step of heating said reinforcing member when applied to said catheter body.

4. The method as set forth in claim 3 wherein the step of applying further includes the step of tensioning the reinforcing member while being applied to said catheter body to cause said reinforcement member to deform the outer surface of said catheter body.

5. The method as set forth in claim 2 wherein the step of applying further includes the step of tensioning the reinforcing member while being applied to said catheter body to cause said reinforcement member to deform the outer surface of said catheter body.

6. The method as set forth in claim 1 wherein the step of applying includes the step of tensioning the reinforcment member while being applied to said catheter body while controlling the tension on said reinforcing member while being applied thereto thus to control the depth of penetration of the reinforcement member beyond the outer surface of said catheter body toward the axis thereof, thereby to control the location of said reinforcement member in said finished catheter.

7. The method as set forth in claim 1 wherein said catheter body is made from a thermoplastic material, and wherein the step of applying includes the step of heating said thermoplastic catheter body sufficient to permit the reinforcing member to cause the outer surface of said catheter body to become irregular when applied thereto.

8. The method as set forth in claim 7 wherein the step of heating includes the step of heating both the thermoplastic catheter body and the reinforcement member while being applied thereto.

9. The method as set forth in claim 1 wherein said catheter body is made from a curable material, said method including the step of curing said catheter body after the application of said reinforcing member thereto.

10. The method as set forth in claim 9 wherein the step of curing is carried out immediately following the step of smoothing.

11. The method as set forth in claim 1 further including the step of periodically excising a selected length of said reinforcement member from said catheter body to form a catheter having spaced reinforced and non-reinforced lengths.

12. The method of claim 1 wherein said reinforcing member is a braid comprising a plurality of reinforcing members applied to said catheter body in a spaced array.

13. The method as set forth in claim 1 wherein the step of applying a reinforcing member further comprises the step of applying a length of reinforcing material at a preselected helix angle to said catheter body relative to its axis.

14. The method as set forth in claim 13 wherein the step of applying said reinforcing member at a preselected helix angle further comprises the step of rotating a guide carrying said reinforcing member in a path approximately normal to the axis of said catheter, the helix angle being defined by the length of movement of the catheter body for each rotation of said guide, and further comprising the step of ceasing rotation of said guide to decrease said helix angle relative to the axis of said catheter to define a length of catheter body in which said reinforcing member lies near the surface thereof during the time the guide has ceased rotating, whereby excision of said reinforcing member from the surface of said catheter may be carried out to excise spaced portions of said reinforcing material from said catheter structure.

15. A method according to claim 1, wherein said reinforcing member is an electrically conductive material adapted as a conductor for electrical signals.

16. A continuous method of making a finished reinforced catheter from a thermoplastic material having an inner diameter and an outer diameter with a single extrusion step and without application of pressure from an external source to said inner diameter comprising the steps of:

continuously extruding a mandrelized catheter body as in interim structure having an outer diameter about equal to the outer diameter of said finished reinforced catheter;

heating said mandrelized catheter body to a temperature to cause said thermoplastic material to exhibit a predetermined degree of viscosity;

continuously applying a tensioned length of a reinforcing member to an outer surface of said heated interim catheter body by a guide rotating in a plane approximately normal to movement of the catheter body to define a helix angle determined by the ratio of the length through which the tube advances for each complete rotation of the guide;

the step of applying being carried out while said catheter body is sufficiently viscous to permit deformation at a surface contour of said catheter body by an amount at least equal to the volume of said reinforcing material embedded and penetration of said reinforcing member through a wall of said catheter body to locate said reinforcing member entirely therein at a location determined by said viscosity and tension on said reinforcing member while the length of reinforcing member is applied thereto; and smoothing the outer surface of said catheter body with said helically wrapped reinforcing member applied thereto to form said finished catheter product, while eliminating a second step of extruding an outer wall portion of a finished catheter product.

17. The method as set forth in claim 16 including the step of ceasing the rotation of said guide to cause said reinforcing member to lie along the surface of said catheter body for a length determined by the time in which rotation in which said guide has ceased relative to the movement of the tube in its axial direction, thereby to facilitate excision of said reinforcing material along said length to form a unitary catheter.

18. A method as set forth in claim 16 further including the step of applying at least a second length of reinforcing material to said catheter body, said first length being applied at a first helix angle which is large relative to the axis of the catheter body, the second length being applied at a small angle relatively to said axis, the application of a multiple set of helices to the catheter body being controlled to produce precise torque and stiffness characteristics for the finished catheter.

19. A method according to claim 16, wherein said reinforcing member is an electrically conductive material adapted as a conductor for electrical signals.

20. The method as set forth in claim 19 further including a smoothing step to smooth the other surface of said elongated product after said reinforcing member has passed therethrough, so that the final surface of the finished product can be developed with a smoothing step while eliminating a requirement for a second extrusion step to produce said final surface of said finished product.

21. A method according to claim 16, wherein said reinforcing member is an electrically conductive material adapted as a conductor for electrical signals.

22. The method of claim 16 wherein said catheter is made from a thermoplastic resin, and the step of applying includes the step of heating said mandrelized catheter body to permit deformation or penetration when said reinforcing member is applied thereto.

23. The method as set forth in claim 22 wherein the step of heating further includes the step of heating said reinforcing member when applied to said catheter body.

24. The method as set forth in claim 23 wherein the step of applying further includes the step of tensioning the reinforcing member while being applied to said catheter body to cause said reinforcement member to deform the outer surface of said catheter body to form said irregular outer surface.

25. The method as set forth in claim 22 wherein the step of applying further includes the step of tensioning the reinforcing member while being applied to said catheter body to cause said reinforcement member to deform the outer surface of said catheter body to form said irregular outer surface.

26. The method as set forth in claim 16 wherein the step of applying includes the step of tensioning the reinforcement member while being applied to said catheter body while controlling the tension on said reinforcing member while being applied thereto thus to control the depth of penetration of the reinforcement member beyond the outer surface of said catheter body toward the axis thereof, thereby to control the location of said reinforcement member in said finished catheter.

27. The method as set forth in claim 16 wherein said catheter body is made from a thermoplastic material, and wherein the step of applying includes the step of heating said thermoplastic catheter body sufficient to permit the reinforcing member to cause the outer surface of said catheter body to become irregular when applied thereto.

28. The method as set forth in claim 27 wherein the step of heating includes the step of heating both the thermoplastic catheter body and the reinforcing member while being applied thereto.

29. The method as set forth in claim 16 wherein said catheter body is made from a curable material, said method including the step of curing said catheter body after the application of said reinforcing member thereto.

30. The method as set forth in claim 29 wherein the step of curing is carried out immediately following the step of smoothing.

31. The method as set forth in claim 16 further including the step of periodically excising a selected length of said reinforcement member from said catheter body to form a catheter having spaced reinforced and non-reinforced lengths.

32. The method of claim 16 wherein said reinforcing member is a braid comprising a plurality of reinforcing members applied to said catheter body in a spaced array.

33. The method as set forth in claim 16 wherein said the step of applying a reinforcing member further comprises the step of applying a length of reinforciing material at a preselected helix angle to said catheter body relative to its axis.

34. The method as set forth in claim 33 wherein the step of applying said reinforcing member at a preselected helix angle further comprising the step of rotating a guide carrying said reinforcing member in a path approximately normal to the axis of said catheter, the helix angle being defined by the length of movement of the catheter body for each rotation of said guide, and further comprising the step of ceasing rotation of said guide to decrease said helix angle relative to the axis of said catheter to define a length of catheter body in which said reinforcing member lies near the surface thereof during the time the guide has ceased rotating, whereby excision of said reinforcing member from the surface of said catheter may be carried out to excise spaced portions of said reinforcing material from said catheter structure.

35. A method of continuously making catheter tubing having an internal bore of accurate dimensions in a single extrusion step without applying pressure from an external source through said internal bore, comprising the steps of:

applying a reinforcing material to a mandrelized tube travelling at a relatively fixed linear rate and having an external diameter about equal to the desired external diameter of catheter tubing, said tube defining an external wall surface and an internal wall surface, to locate said reinforcing material within said tube at any location intermediate said external and said internal wall surfaces, the applying step being carried out while said tube is sufficiently heated to exhibit a viscosity at said linear rate sufficient to permit said reinforcement material to travel under tension from a location external to said exterior wall surface to said predetermined location within said tube, the temperature of said tube and the tension on said reinforcing material being selected to cooperate to carry out effectively said applying step for the material of said tube when traveling at said linear rate, causing said tube with said reinforcement embedded therein to cool sufficiently to solidify, thus to embed said reinforcement therein; and smoothing the exterior surface of said tube while traveling at said linear rate with said reinforcement therein to a smooth surface finish with a tolerance such as ±0.0005 inches which is suitable for use in catheters, said smoothing step following said cooling step without an interventing step of extruding another layer of tubing on said reinforcement tubing, thereby to form reinforced catheters, said smoothing step following said cooling step without an intervening step of extruding another layer of tubing on said reinforcement tubing thereto to form reinforced catheter stock.

* * * * *